(12) United States Patent
Huang

(10) Patent No.: US 6,790,165 B2
(45) Date of Patent: Sep. 14, 2004

(54) REHABILITATION AID

(75) Inventor: Tien-Wang Huang, Taipei (TW)

(73) Assignees: Chih-Hung Huang, Taipei (TW);
Chia-Yin Huang, Taipei (TW)

( * ) Notice: Subject to any disclaimer, the term of this patent is extended or adjusted under 35 U.S.C. 154(b) by 227 days.

(21) Appl. No.: 10/232,395

(22) Filed: Sep. 3, 2002

(65) Prior Publication Data

US 2004/0043879 A1 Mar. 4, 2004

(51) Int. Cl.[7] .............................................. A63B 23/10
(52) U.S. Cl. ........................ 482/79; 482/80; 482/907; 602/27
(58) Field of Search ............................ 602/23–28; 2/16, 2/22; 482/907, 79, 80, 124, 105, 128, 136, 145, 146

(56) References Cited

U.S. PATENT DOCUMENTS

| | | | | |
|---|---|---|---|---|
| 2,467,943 A | * | 4/1949 | Mikell, Jr. | |
| 2,498,006 A | * | 2/1950 | Ridill | |
| 4,955,370 A | * | 9/1990 | Pettine | |
| 5,382,224 A | * | 1/1995 | Sprangler | |
| 5,662,595 A | * | 9/1997 | Chesher et al. | |
| 5,683,336 A | * | 11/1997 | Pape | |
| 6,602,217 B2 | * | 8/2003 | Crawford et al. | |

* cited by examiner

Primary Examiner—Jerome W. Donnelly
(74) Attorney, Agent, or Firm—Birch, Stewart, Kolasch & Birch, LLP

(57) ABSTRACT

A rehabilitation aid includes a leg sleeve, an adjusting means connected to a front side of the leg sleeve, a spring connected at an end to the adjusting means, and a foot strap connected to another end of the spring. The leg sleeve and the foot strap are designed for adjustably putting around a user's leg close to a lower part thereof and the user's sole close to the toes, respectively. The spring is adapted to generate a pulling stress suitable for the user through control of the adjusting means, so that the user's toes and ball of the foot are raised along with the user's heel via an upward angular pulling force provided by the spring to protect the user from tripping and falling during practicing walking alone.

3 Claims, 5 Drawing Sheets

REHABILITATION AID

FIELD OF THE INVENTION

The present invention relates to a rehabilitation aid that has simple structure to effectively protect a apoplectic from tripping and falling during practicing walking alone without using a crutch or other type of big-volume supportive device, and therefore helps the apoplectic to rebuild his or her faith and confidence to restore to health more quickly.

BACKGROUND OF THE INVENTION

People's living standards are largely upgraded with the highly developed social and economic prosperity. As a result, a lot of people are suffering from many physical problems, such as hypertension and cerebral apoplexy, caused by taking in too much food containing high calorie and cholesterol. The age bracket of apoplectics has gradually lowered. Many people, who suddenly suffer from cerebral apoplexy, become passive or hot-tempered. Hospitals and/or health centers have to take care these patients not only to rebuild their faith and confidence, bust also provide good rehabilitation treatments. Rehabilitation treatments would usually continue for a considerably long time period and be conducted at specific locations with particularly designed apparatus. It is a tough work for most apoplectics to go to hospitals and health centers, particularly when the patients have difficulty in walking, because their toes and ball of the foot have poor blood circulation and normally fail to move upward along with their heel during walking. That is why the apoplectics frequently trip and fall. To protect the apoplectics against such tripping and falling, hospitals and health centers usually provide specially designed rehabilitation lanes for the patients to train their legs. However, since there are only limited numbers of rehabilitation apparatus available for use, and since it is not convenient for the patients to go to hospitals frequently, the patients would generally use a crutch or some other supportive devices to practice walking at home or around nearby parks. These supportive devices usually have a big volume to occupy a considerably large space to possibly interfere and/or collide with other people and cause undesired tripping and falling of the patients.

It is therefore desirable to develop a structurally simple rehabilitation aid to help an apoplectic to practice walking alone without the risk of tripping and falling.

SUMMARY OF THE INVENTION

A primary object of the present invention is to provide a rehabilitation aid that enables an apoplectic to walk freely without using any big-volume supportive device, and thereby helps the patient to rebuild his faith and confidence and speeds up the restoration of the patient's health.

Another object of the present invention is to provide a rehabilitation aid that helps an apoplectic to move his toes and ball of the foot upward along with a raised heel to avoid tripping and falling.

A further object of the present invention is to provide a rehabilitation aid that includes adjusting means to enable a user to control a pulling stress to be generated by a spring to pull the user's toes upward depending on the user's actual leg condition.

A still further object of the present invention is to provide a rehabilitation aid that has simple structure and occupies only very small space, and is designed for wearing on a user's leg to help the user to walk freely and safely.

To achieve the above and other objects, the rehabilitation aid of the present invention mainly includes a leg sleeve, an adjusting means connected to a front side of the leg sleeve, a spring connected at an end to the adjusting means, and a foot strap connected to another end of the spring. The leg sleeve and the foot strap are designed for adjustably putting around a user's leg close to a lower part thereof and the user's sole close to the toes, respectively. The spring is adapted to generate a pulling stress best suitable for the user through control of the adjusting means, so that the user's toes and ball of the foot are raised along with the user's heel via an upward angular pulling force provided by the spring to protect the user from tripping and falling during practicing walking alone.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
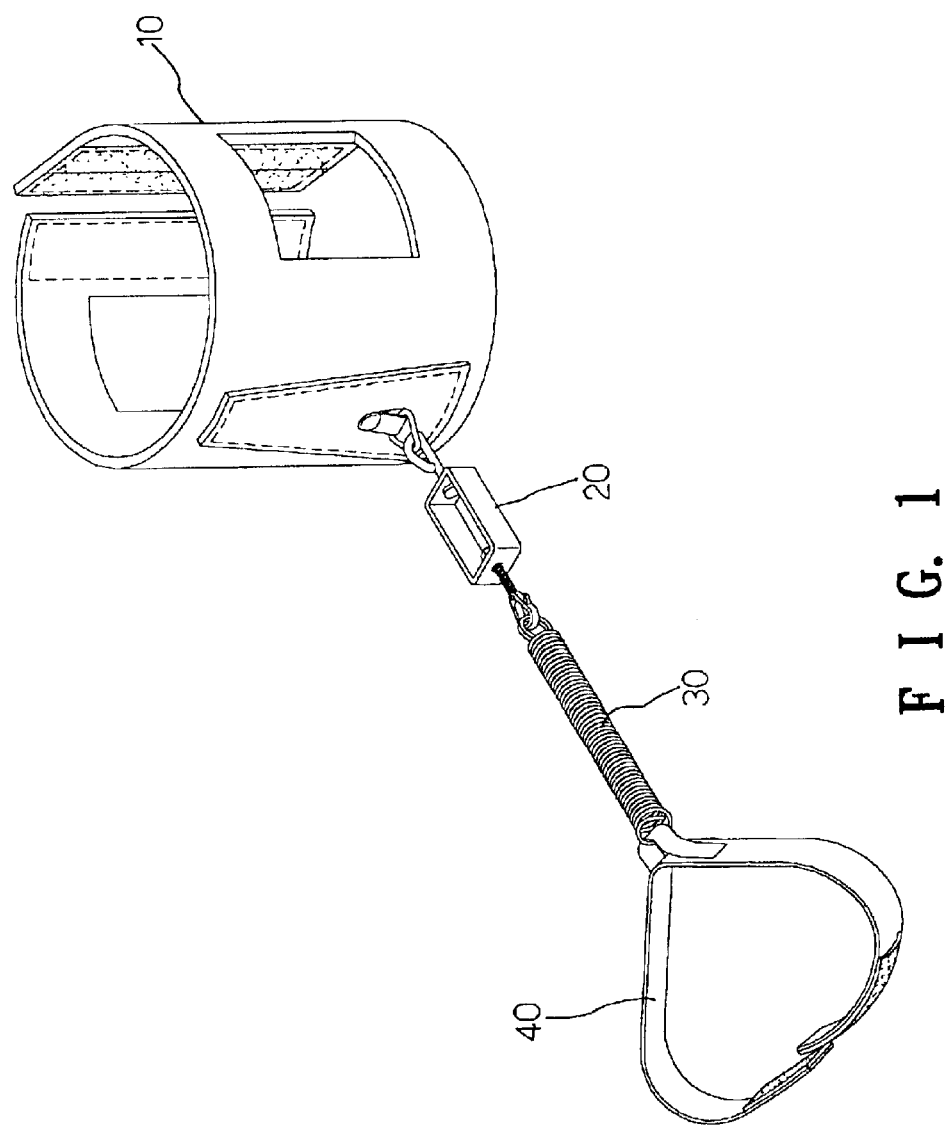
FIG. 1 is an assembled perspective view of a rehabilitation aid according to an embodiment of the present invention.

Please refer to FIG. 1 that is an assembled perspective view of a rehabilitation aid according to an embodiment of the present invention. As shown, the rehabilitation aid mainly includes a leg sleeve 10, an adjusting means 20, a spring 30, and a foot strap 40. The leg sleeve 10 is designed for putting around a user's shank at a predetermined position, and the foot strap 40 is for surrounding the user's sole close to toes. The adjusting means 20 has an end connected to the leg sleeve 10 and another end to an end of the spring 30, and the other end of the spring 30 is connected to an end of the foot strap 40 to provide a simple and continuous structure. By controlling the adjusting means 20, the spring 30 may have a pulling stress meeting an individual user's need, so that the spring 30 of the rehabilitation aid in use yields an angularly upward pull force.

Figure 2:
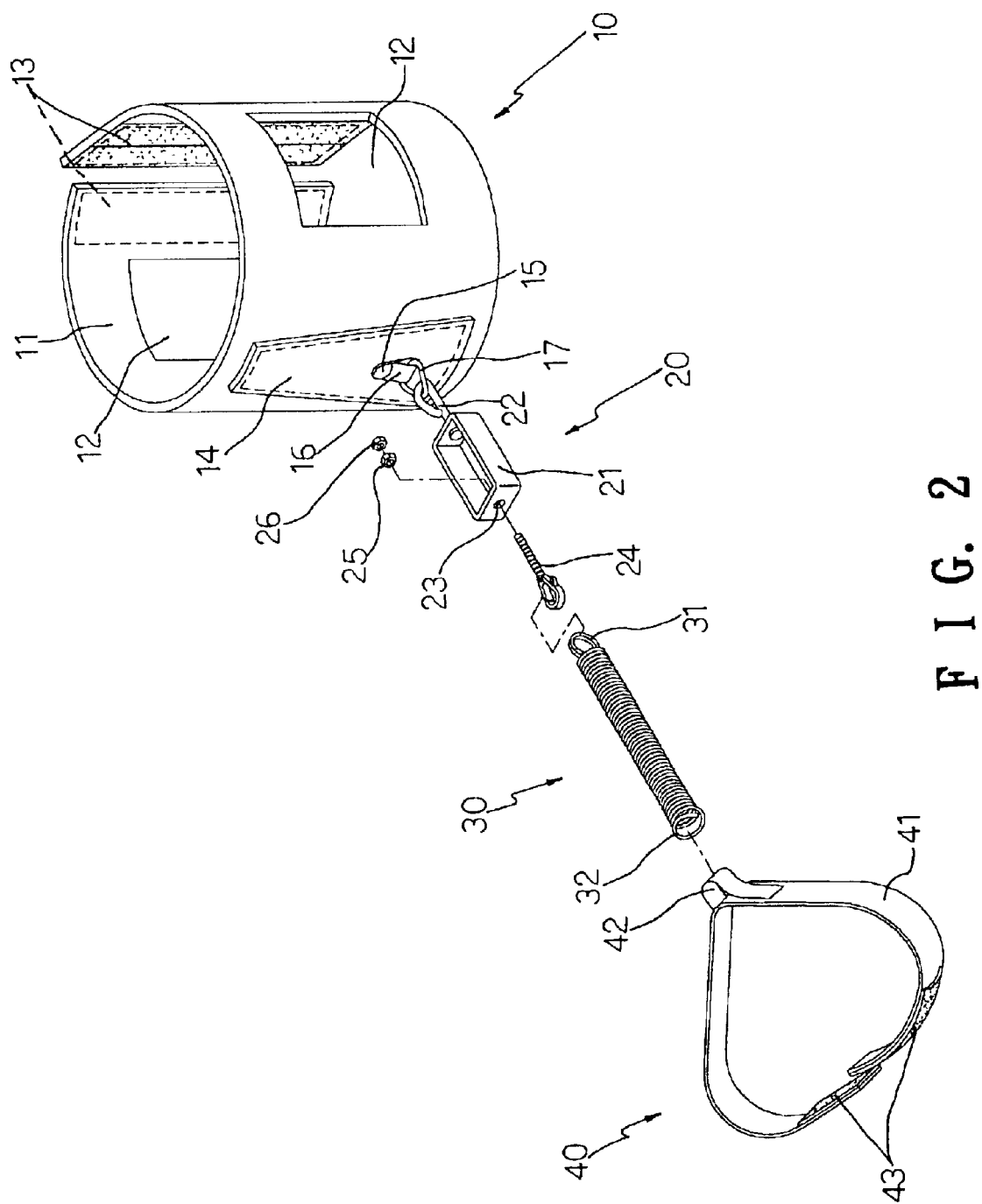
FIG. 2 is an exploded perspective view of FIG. 1.

Please refer to FIG. 2 that is an exploded perspective view of FIG. 1. As shown, the leg sleeve 10 of the rehabilitation aid of the present invention shown in FIGS. 1 and 2 has a main body 11, at two generally diametrically opposite sides of which two venting openings 12 are formed. Two free ends of the main body 11 are provided with repeatedly usable fastening means 13, such as magic tapes consisting of a loop and a hook tape, so that the user may fitly wrap and locate the leg sleeve 10 around a leg through the magic tapes 13. The venting openings 12 provide good air ventilating effect to enable comfortable wearing of the leg sleeve 10. A connecting piece 14 is sewed onto the main body 11 of the leg sleeve 10 at a front outer surface located between the two venting openings 12. A rivet 15 is fixed to a lower part of the connecting piece 14 to rivet a loop 16 to the leg sleeve 10.

An angle ring 17 is extended through and thereby connected to the loop 16 for connecting with the adjusting means 20.

The adjusting means 20 includes a frame member 21, an integrally formed swivel hook 22 having a straight end movably connected to an end of the frame member 21 facing toward the leg sleeve 10 and another bent end extended through the angle ring 17 to connect thereto, a hole 23 provided on another end of the frame member 21 opposite to the swivel hook 22, a holder 24 having a screw-rod body adapted to extend through the hole 23 and an openable retaining ring connected to an end of the screw-rod body for connecting to an end of the spring 30, an adjusting nut 25 screwed to the screw-rod body of the holder 24 for axially adjusting the holder 24 relative to the frame member 21, and a stop nut 26 screwed to the screw-rod body of the holder 24 for tightening the holder 24 to the frame member 21 without separating therefrom. The user may use the adjusting means 20 to adjust a pull force between the leg sleeve 10 and the foot strap 40 of the rehabilitation aid according to personal need.

The spring 30 has an end in the form of a closed ring 31 for engaging with the openable retaining ring of the holder 24 of the adjusting means 20, and another end in the form of an open coil 32 adapted to serve as a hook for hooking up the foot strap 40.

The foot strap 40 is formed from a belt 41 having a constant width. The belt 41 is provided at two free ends with repeatedly usable fastening means, such as magic tapes 43 consisting of a hook and a loop tape. A loop 42 is sewed onto a middle outer surface of the belt 41 for engaging with the open coil 32 of the spring 30.

The whole rehabilitation aid of the present invention may be adjusted according to the user's individual need or rehabilitation progress for the spring 30 to generate an appropriate pulling stress, so that the user, who is usually an apoplectic, gradually gets well from a stroke to walk freely and safely through use of the rehabilitation aid without depending on other types of big-volume supportive devices. The rehabilitation aid of the present invention helps the apoplectic to rebuild faith and confidence to more quickly restore to health.

Figure 3:
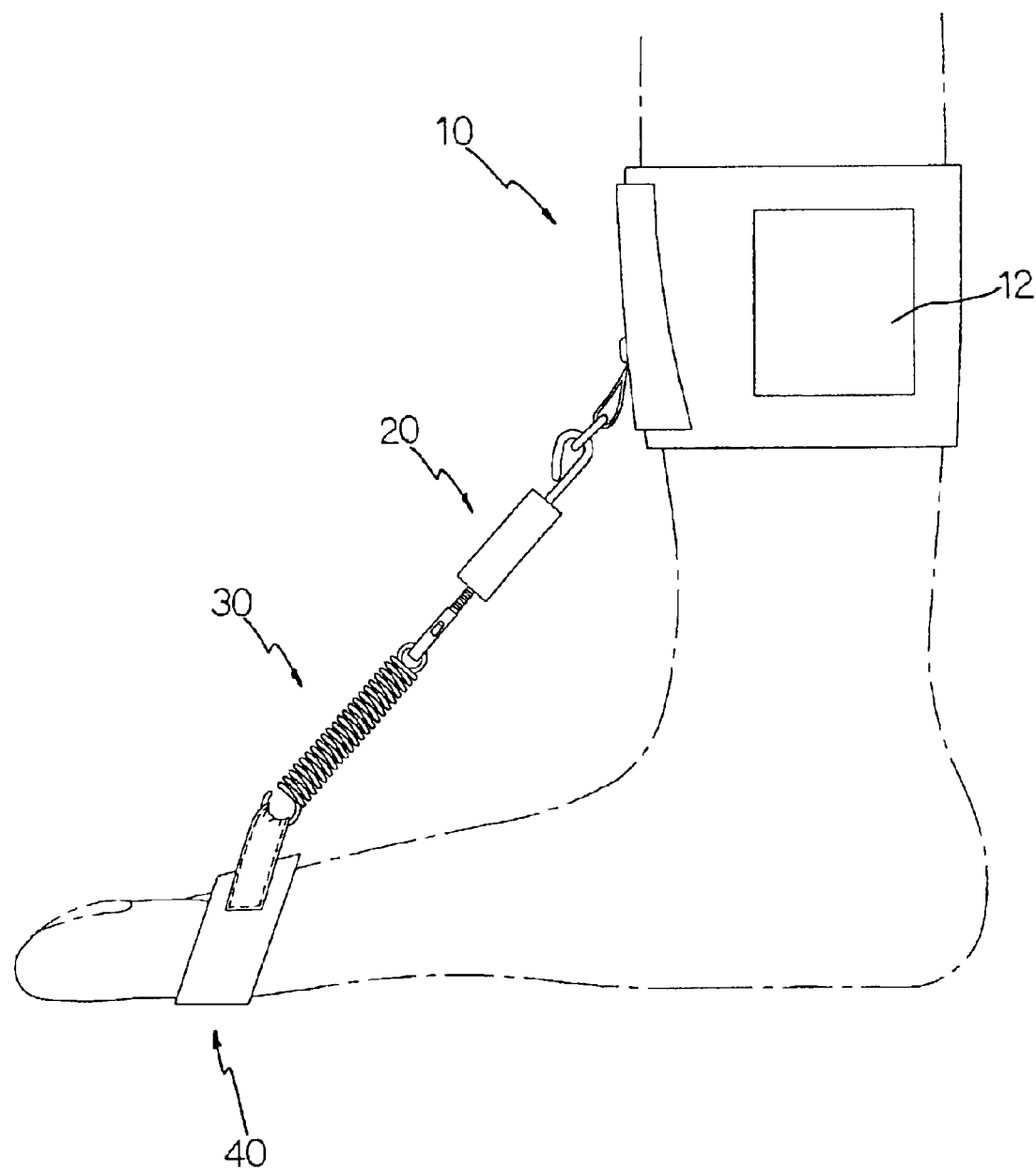
FIG. 3 shows the rehabilitation aid of the present invention being worn on a user's foot.

FIG. 3 shows the rehabilitation aid of the present invention worn on an apoplectic's foot for use. To wear the rehabilitation aid, first put the leg sleeve 10 around the user's leg close to a lower part thereof. With the magic tapes 13 provided at two free ends of the leg sleeve 10, the user may conveniently adjust the leg sleeve 10 to a desired tightness around the leg. The venting openings 12 at two sides of the leg sleeve 10 enable comfortable wearing of the leg sleeve 10 on the user's leg. Thereafter, put the foot strap 40 around the user's sole close to the toes. Similarly, the user may conveniently use the magic tapes 43 provided at two free ends of the foot strap 40 to adjust the latter to a most suitable tightness around the sole. The adjusting means 20 and the spring 30 continuously extended between the leg sleeve 10 and the foot strap 40 together provides an upward angular pull force. A magnitude of the pull force may be adjusted and set via the adjusting means 20 depending on the user's actual physical condition to effectively speed up the rehabilitation of the user.

Figure 4:
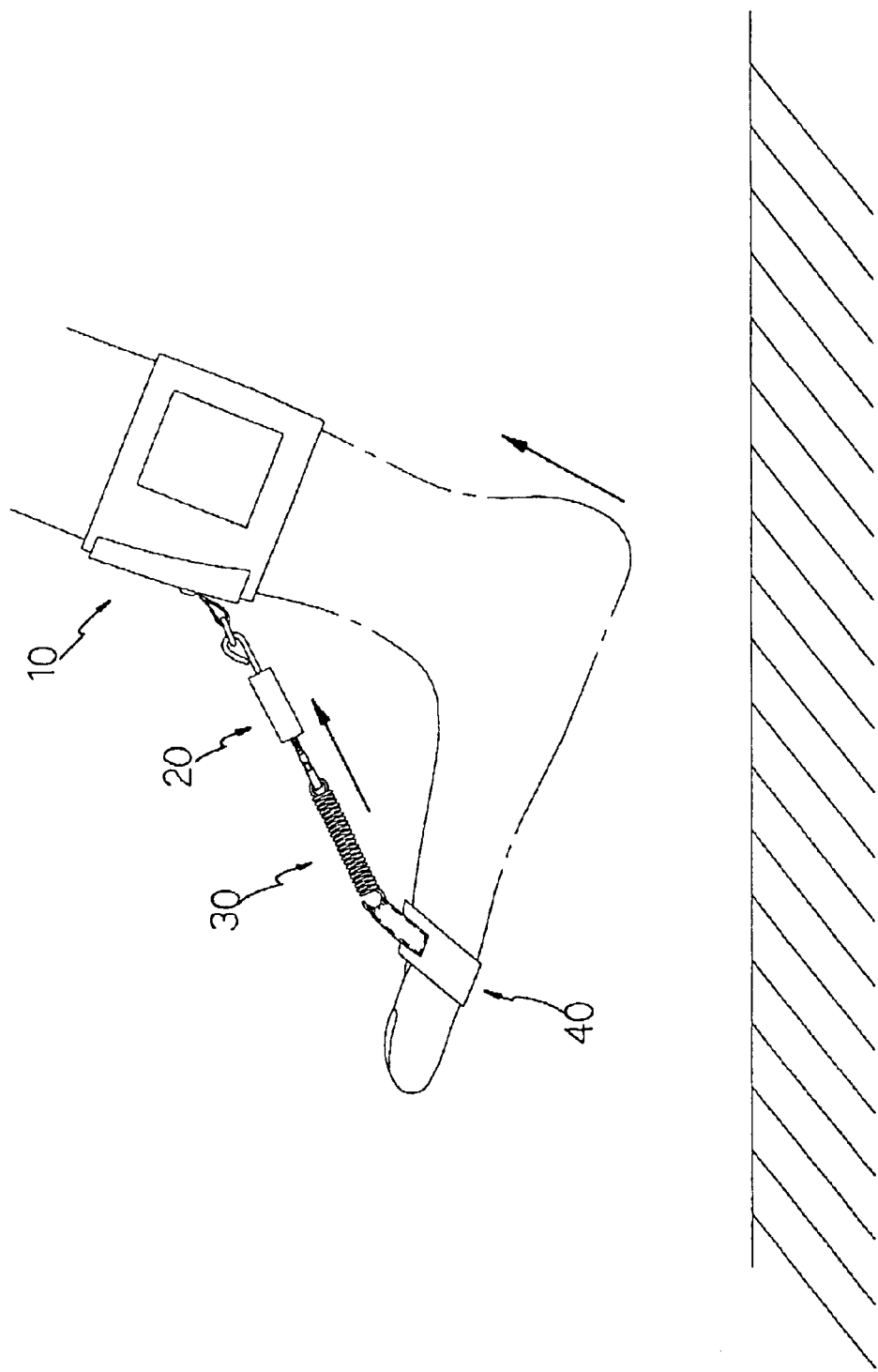
FIG. 4 shows the movement of a user's foot wearing the rehabilitation aid of the present invention.

FIG. 4 shows the movement of an apoplectic's foot wearing the rehabilitation aid of the present invention. As mentioned before, the leg sleeve 10 is put around a lower part of the leg, the foot strap 40 is put around the sole close to the toes, and the adjusting means 20 and the spring 30 connect the leg sleeve 10 to the foot strap 40 to generate a suitably adjusted pulling stress. When the user practices walking by wearing the rehabilitation aid of the present invention on the leg, the pulling stress generated by the spring 30 enables the user's toes and ball of the foot to move upward along with a raised heel, protecting the user from tripping and falling during walking.

Figure 5:
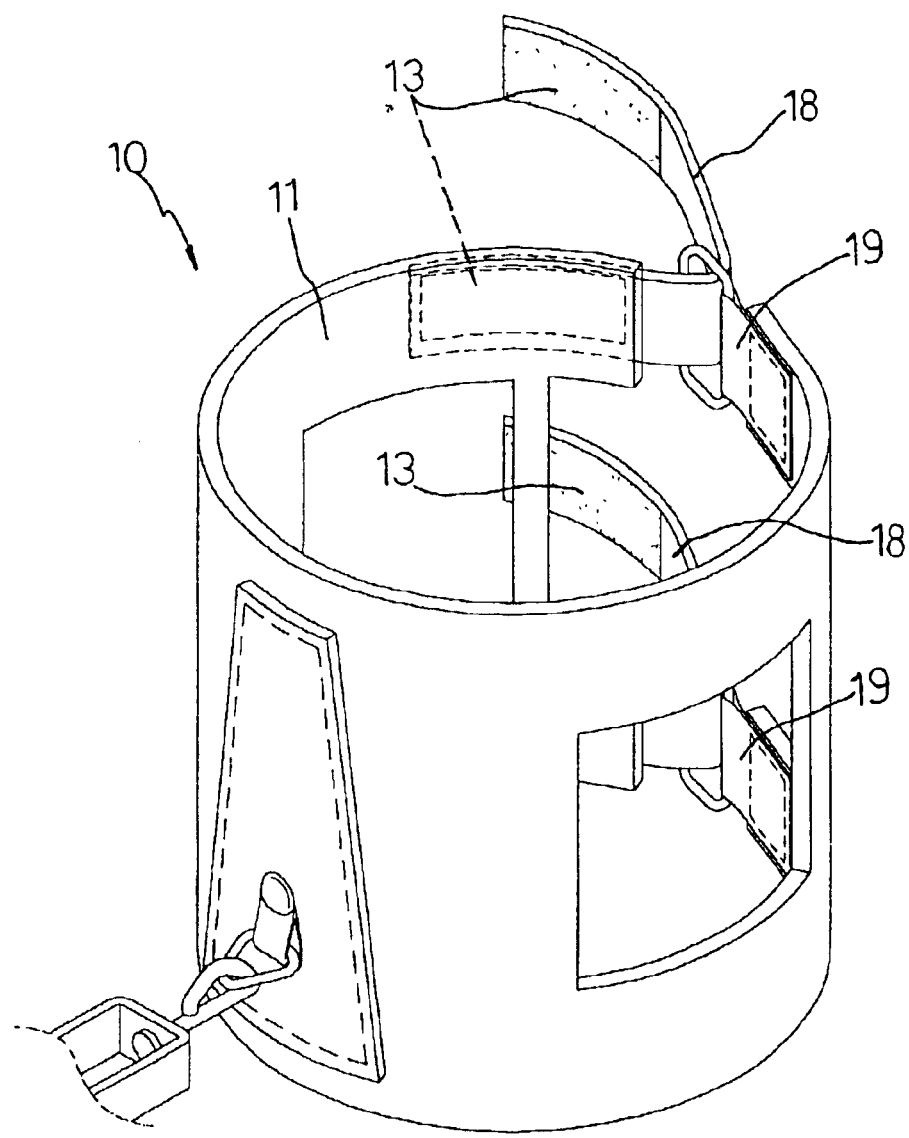
FIG. 5 is a fragmentary perspective view of a rehabilitation aid according to another embodiment of the present invention.

FIG. 5 shows a leg sleeve 10 according to another embodiment of the present invention. In this embodiment, fastening means in the form of matching belt 18 and buckle 19 are used in place of the hook and the loop tape of the magic tapes 13 directly attached to the free ends of the leg sleeve 10. The belt 18 has a constant width and has an end sewed onto one free end of the main body 11 of the leg sleeve 10. It is preferably two belts 18 are provided to vertically space apart on the free end of the main body 11. Again, hook tapes and loop tapes of magic tapes 13 are provided at two free ends of the belts 18. The buckles 19 are sewed onto another free end of the main body 11 corresponding to the belts 18. By extending free ends of the belts 18 through the buckles 19 and attaching them to the other ends of the belts 18 sewed onto the main body 11, the leg sleeve 10 may be put around the user's leg with suitably adjusted tightness.

The present invention has been described with a preferred embodiment thereof and it is understood that many changes and modifications in the described embodiment can be carried out without departing from the scope and the spirit of the invention as defined by the appended claims.

What is claimed is:

1. A rehabilitation aid, comprising:

a leg sleeve having a main body, at two generally diametrically opposite sides of which two venting openings are formed, and at two free ends of which repeatedly usable fastening means are provided; a connecting piece sewn onto a front outer surface of said main body located between said two venting openings; a rivet fixed to a lower part of said connecting piece to rivet a loop to said leg sleeve; and an angle ring extended through and thereby connected to said loop;

an adjusting means including a frame member, an integrally formed swivel hook having a straight end movably connected to an end of said frame member facing toward said leg sleeve and another bent end extended through said angle ring of said adjusting means to connect thereto, a hole provided on another end of said frame member opposite to said swivel hook, a holder having a screw-rod body adapted to extend an end through said hole on said frame member and an openable retaining ring connected to another end of said screw-rod body, an adjusting nut screwed to said screw-rod body of said holder for axially adjusting said holder relative to said frame member, and a stop nut screwed to said screw-rod body of said holder for fixing said holder to said frame member without separating therefrom;

a spring having an end in the form of a closed ring for engaging with said openable retaining ring of said holder of said adjusting means, and another end in the form of an open coil adapted to serve as a hook; and a foot strap formed from a belt having a constant width, said belt being provided at two free ends with repeatedly usable fastening means, and a loop sewn, onto a middle outer surface of said belt for engaging with said open coil of said spring;

said spring being adapted to generate an appropriate pulling stress through control of said adjusting means to meet an apoplectic's individual need or progress of physical conditions, so that said leg sleeve and said foot strap work together to raise the apoplectic's toes and ball of the foot and the heel at the same time to protect the apoplectic from tripping and falling.

2. The rehabilitation aid as claimed in claim 1, wherein said fastening means provided on said leg sleeve comprises a loop and a hook tape directly sewed onto free ends of said main body of said leg sleeve.

3. The rehabilitation aid as claimed in claim 1, wherein said fastening means provided on said leg sleeve comprises belts and matching buckles, and said belts further including loop and a hook tape.

* * * * *